United States Patent [19]

Christen et al.

[11] 4,026,986

[45] May 31, 1977

[54] CAPSULE SHELL

[75] Inventors: Jimmie Duane Christen, Clute, Tex.; Wen-Jiu Cheng, Midland, Mich.

[73] Assignee: The Dow Chemical Company, Midland, Mich.

[22] Filed: May 22, 1975

[21] Appl. No.: 580,116

[52] U.S. Cl. .................. 264/301; 264/DIG. 37; 427/2
[51] Int. Cl.[2] .................. B29C 13/00; B29C 13/04
[58] Field of Search ......... 427/430, 435, 385, 388, 427/2, 3; 106/210; 264/301, DIG. 37; 425/269

[56] References Cited

UNITED STATES PATENTS

| | | | |
|---|---|---|---|
| 2,299,039 | 10/1942 | Scherer | 264/301 |
| 3,378,546 | 4/1968 | Tsuzuki | 106/210 X |
| 3,493,407 | 2/1970 | Greminger et al. | 264/301 X |
| 3,617,588 | 11/1971 | Langman | 264/301 X |

*Primary Examiner*—James R. Hoffman
*Attorney, Agent, or Firm*—David B. Kellom

[57] ABSTRACT

Capsule shells for pharmaceutical use are presently made from gelatin. Use of water-soluble starch ethers instead of gelatin facilitates the production of the shells and produces improved shells. Preferred material is 2-hydroxypropyl starch made from high-amylose starch and having about 0.3 to 2.5 hydroxypropyl groups per glucose unit of the starch.

3 Claims, No Drawings

CAPSULE SHELL

BACKGROUND OF THE INVENTION

Heretofore pharmaceutical capsule shells (hereinafter "capsules") have been made almost exclusively from gelatin. In a carefully controlled process, metal pins of the desired dimensions are dipped into an aqueous solution of gelatin and then slowly withdrawn, the gelatin coating thus deposited, when dried, forming one half of a capsule. To achieve uniformity in the capsules, the gelatin should be as pure and uniform as possible, the solution used for the dipping should be at a carefully controlled concentration, viscosity and temperature and the pins should be at the proper temperature and should be withdrawn at rate corresponding to a predetermined schedule.

Gelatin, being a natural product, varies in molecular weight and viscosity, depending on its source and previous history, and it is becoming increasingly difficult to obtain adequate supplies having the necessary purity and uniformity. Many other water-soluble polymers, such as cellulose ethers, have been proposed to replace gelatin but none has been commercially successful.

SUMMARY OF THE INVENTION

It has now been found that uniform and satisfactory capsules can be made from certain hydroxyalkyl starches and that appropriate aqueous solutions of such starch ethers can be substituted for gelatin solutions in the highly automated capsule-forming processes now used to make capsules with only minor modifications in the process. Such solutions can be prepared on a commercial scale with greater uniformity than gelatin solutions and are less subject to microbial contamination and deterioration than the latter due to the hydroxypropyl substitution.

DETAILED DESCRIPTION OF THE INVENTION

The hydroxyalkyl starches (hereinafter HAS) include hdroxyethyl starch, 2-hydroxypropyl starch and the mixed ethers, such as hydroxyethyl methyl and 2-hydroxypropyl methyl starch. The etherifying groups must be of such nature, and present in such proportions, that the HAS is water-soluble and a 2%, by weight, aqueous solution thereof will have an Ubbelohde viscosity at 20° C. of about 2–15 cps. (Preferably 3–5 cps). These properties also require that the starch used in its preparation contain at least about 50% of substantially linear starch (amylose). The dipping bath used in making the capsules should contain about 20 to 45% of HAS and should have a viscosity of about 500–10,000 cps. (Preferably about 750–1250 cps.) (Brookfield, No. 2 spindle at 12 rmp).

The starch ethers are well known materials and are conveniently made by the reaction of starch with alkali and one or more etherifying agents, such as alkyl halides and alkyene oxides.

The equipment and techniques used for making capsules from gelatin are suitable for use with starch ethers. One advantage of the latter materials is that they are chemically more stable in aqueous solutions and can be used at higher temperatures. This permits the use of more concentrated solutions and results in faster drying, thus increasing production. Another advantage is that the higher temperatures that can be used discourage microbial contamination of the dipping bath, thus alleniating a major problem in the industry.

The starch ethers of the invention are compatible with gelatin, carboxymethyl, cellulose, carboxymethyl starch and similar carbohydrate ethers, esters and ether-esters, as well as pharmaceutically acceptable plasticizers for such materials, such as glycerol and partial esters of glycerol with acetic acid or the like. Accordingly, capsule shells can be made according to the invention by use of blends of starch ethers with such materials.

The following example illustrates the practice of the invention.

Corn starch consisting of about 75% amylose and 25% of amylopectin was oxypropylated by reaction with NaOH and propylene oxide the "molar substitution" (MS), i.e., moles of propylene oxide reacted per glucose unit in the starch being about 1.6 (30% by wt.). A 2% aqueous solution of the hydroxypropyl starch (HPS) had an Ubbelohde viscosity at 20° C. of 3.46 cps. and a 27.3% aqueous solution (dipping bath) had a Brookfield viscosity (No. 2 spindle at 6 rpm) of 1430 cps. at 63.5° C., the dipping temperature used.

Capsule dipping pins of stainless steel, ¼ inch by 1½ inches, were dipped into the bath and withdrawn in 20 seconds at a constant rate of withdrawal. After being dried at room temperature the half-capsules were removed from the pins and found to be clear and highly uniform with a thickness of about 4.6 mils and a weight of about 40–50 mg.

We claim:

1. In the process for making pharmaceutical capsules by dip-coating pins in an aqueous dip bath of a water-soluble film-forming material, withdrawing the coated pins and drying to form one half of a capsule, the improvement wherein the bath is essentially an aqueous solution of hydroxyalkyl starch having an Ubbelohde viscosity of about 2–15 cps as a 2 percent aqueous solution at 20° C.

2. The process of claim 1 wherein the hydroxyalkyl starch is 2-hydroxypropyl starch.

3. The process of claim 1 wherein the hydroxypropyl starch is made from starch containing at least about 50% of amylose starch.

* * * * *